(12) United States Patent
Goodnow et al.

(10) Patent No.: US 7,545,272 B2
(45) Date of Patent: Jun. 9, 2009

(54) RF TAG ON TEST STRIPS, TEST STRIP VIALS AND BOXES

(75) Inventors: Timothy T. Goodnow, Pleasanton, CA (US); Lei (Lawrence) He, Moraga, CA (US)

(73) Assignee: TheraSense, Inc., Alameda, CA (US)

( * ) Notice: Subject to any disclaimer, the term of this patent is extended or adjusted under 35 U.S.C. 154(b) by 495 days.

(21) Appl. No.: 11/350,398

(22) Filed: Feb. 7, 2006

(65) Prior Publication Data

US 2006/0226985 A1 Oct. 12, 2006

Related U.S. Application Data

(60) Provisional application No. 60/650,912, filed on Feb. 8, 2005, provisional application No. 60/701,654, filed on Jul. 21, 2005.

(51) Int. Cl.
*G08B 13/14* (2006.01)

(52) U.S. Cl. .............. 340/572.1; 340/572.8; 340/573.1; 600/347; 422/82.01

(58) Field of Classification Search .............. 340/572.2, 340/572.1, 573.1, 573.4, 539.12, 539.1, 539.17, 340/568.1, 572.8; 600/365, 347; 204/403.1; 422/82.01

See application file for complete search history.

(56) References Cited

U.S. PATENT DOCUMENTS

| | | | |
|---|---|---|---|
| 5,472,317 A | 12/1995 | Field et al. |
| 5,489,414 A | 2/1996 | Schreiber et al. |
| 5,601,435 A | 2/1997 | Quy |
| D393,313 S | 4/1998 | Meisner et al. |
| 5,735,285 A | 4/1998 | Albert et al. |
| 5,899,855 A | 5/1999 | Brown |
| 5,961,451 A | 10/1999 | Reber et al. |
| 6,159,147 A | 12/2000 | Lichter et al. |
| 6,283,761 B1 | 9/2001 | Joao |
| 6,348,640 B1 | 2/2002 | Navot et al. |
| 6,359,444 B1 | 3/2002 | Grimes |
| 6,560,471 B1 | 5/2003 | Heller et al. |
| 6,942,518 B2 | 9/2005 | Liamos et al. |
| 7,041,468 B2 | 5/2006 | Drucker et al. |

(Continued)

FOREIGN PATENT DOCUMENTS

WO WO-2005/119524 12/2005

(Continued)

OTHER PUBLICATIONS

Internet printout: http:rfid-handbook.com, printed Feb. 6, 2006.

(Continued)

*Primary Examiner*—Anh V La
(74) *Attorney, Agent, or Firm*—SF Bay Area Patents, LLC; Andrew V. Smith

(57) ABSTRACT

A glucose monitoring system, includes a glucose sensor strip or package of strips. The strip includes a substrate and a glucose monitoring circuit that has electrodes and a bodily fluid application portion of selected chemical composition. An antenna is integrated with the glucose sensor strip. A RFID sensor chip is coupled with the glucose sensor strip and the antenna. The chip has a memory containing digitally-encoded data representing calibration and/or expiration date information for the strip.

52 Claims, 9 Drawing Sheets

U.S. PATENT DOCUMENTS

| | | | |
|---|---|---|---|
| 7,049,962 B2 * | 5/2006 | Atherton et al. | 340/572.1 |
| 7,278,983 B2 | 10/2007 | Ireland et al. | |
| 2002/0128594 A1 | 9/2002 | Das et al. | |
| 2003/0023461 A1 | 1/2003 | Quintanilla et al. | |
| 2003/0032867 A1 | 2/2003 | Crothall et al. | |
| 2003/0212379 A1 | 11/2003 | Bylund et al. | |
| 2004/0054263 A1 | 3/2004 | Moerman et al. | |
| 2004/0122353 A1 | 6/2004 | Shahmirian et al. | |
| 2004/0135684 A1 | 7/2004 | Steinthal et al. | |
| 2004/0254434 A1 | 12/2004 | Goodnow et al. | |
| 2005/0003470 A1 | 1/2005 | Nelson et al. | |
| 2005/0023137 A1 * | 2/2005 | Bhullar et al. | 204/403.1 |
| 2005/0239156 A1 | 10/2005 | Drucker et al. | |
| 2005/0277164 A1 | 12/2005 | Drucker et al. | |
| 2005/0281706 A1 * | 12/2005 | Funke et al. | 422/63 |
| 2006/0010098 A1 | 1/2006 | Goodnow et al. | |

FOREIGN PATENT DOCUMENTS

WO    WO 2006/086423 A2    8/2006

OTHER PUBLICATIONS

Internet printout: http:rfid-handbook.com, printed Feb. 7, 2006.
International Search Report for International Patent Application No. PCT/US2006/004355 filed Feb. 8, 2006 to TheraSense, Inc.
International Preliminary Report on Patentability and Written Opinion of the International Searching Authority for International Patent Application No. PCT/US2006/004355 filed Feb. 8, 2006 to TheraSense, Inc.
U.S. Appl. No. 11/112,671, filed Apr. 21, 2005.
U.S. Appl. No. 11/146,897, filed Jun. 6, 2005.

* cited by examiner

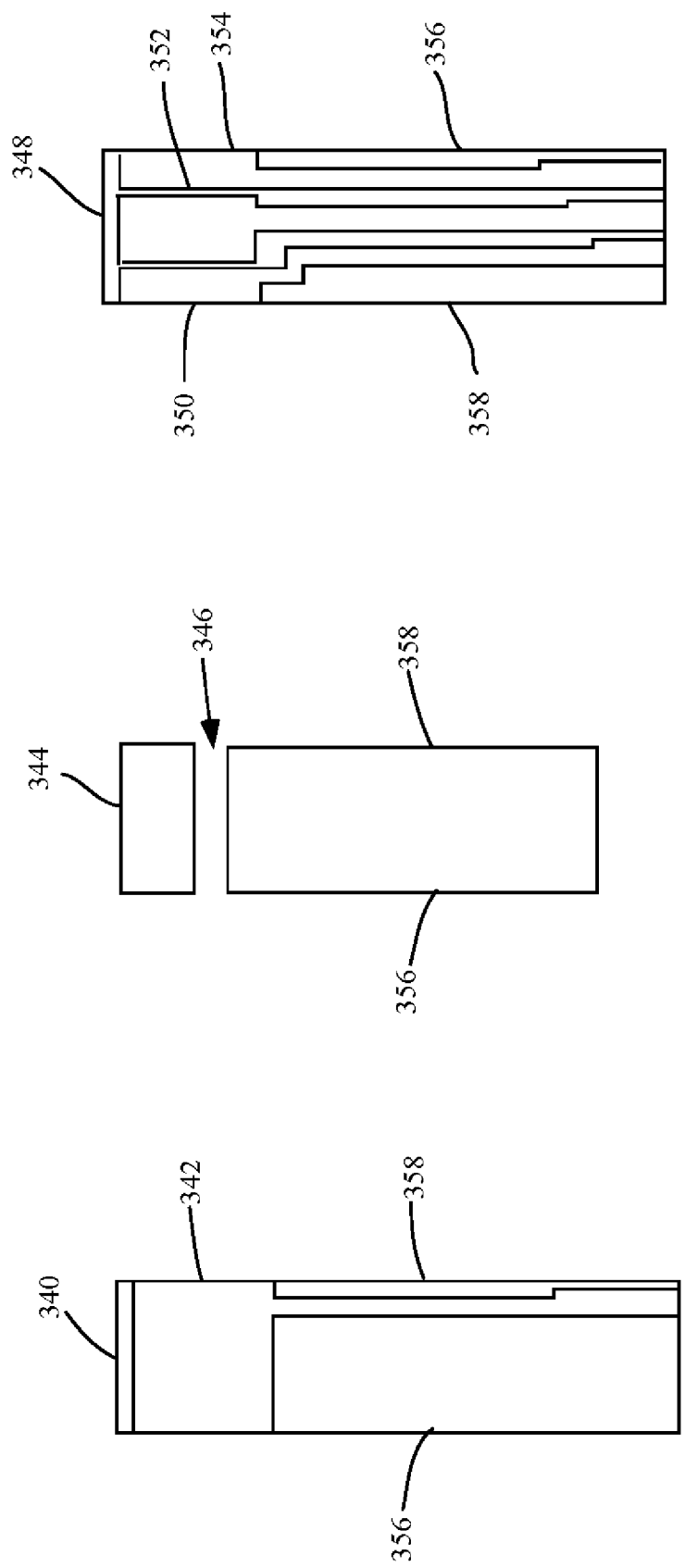

RF TAG ON TEST STRIPS, TEST STRIP VIALS AND BOXES

PRIORITY

This application claims the benefit of priority to U.S. provisional patent applications Nos. 60/650,912, filed Feb. 8, 2005 and 60/701,654, filed Jul. 21, 2005, which are incorporated by reference.

BACKGROUND

Diabetes care involves periodically checking the blood glucose level of a bodily fluid such as blood. Based on the measured bodily fluid level, a diabetic may take one or more steps such as injecting insulin or consuming carbohydrates to bring the level back to a desired level.

Glucose Meters

FIG. 1 illustrates a conventional blood glucose meter 100 (see U.S. Design Pat. No. D393,313, which is hereby incorporated by reference). The meter 100 includes a test strip slot 102, a display 104 and one or more operational buttons 106. Although not shown in FIG. 1, the meter 100 also includes component circuitry for receiving signals that depend on the glucose level of a fluid applied to a strip that is inserted into the slot 102, and component circuitry for determining the glucose level based on the received signals. FIG. 2 illustrates a blood glucose meter 200 with display 104 and operational buttons 106, and also having a glucose test strip 202 inserted into a slot 102 for testing a body fluid sample applied to the strip 202.

Glucose Sensors

Small volume (e.g., less than 0.5 microliter), in vitro, electrochemical sensors are used with Freestyle® and Freestyle Flash™ glucose meters (see http://abbottdiabetescare.com, which is hereby incorporated by reference). These test strip sensors generally include a working electrode on a first substrate, a counter (or counter/reference) electrode on a second substrate, and a sample chamber. The sample chamber is configured so that when a sample (e.g., of blood) is provided in the chamber, the sample is in electrolytic contact with both the working electrode, the counter electrode and any reference electrodes or indicator electrodes that may be present. This allows electrical current to flow between the electrodes to effect the electrolysis (electrooxidation or electroreduction) of the analyte. A spacer is generally positioned between first substrate and second substrate to provide a spacing between electrodes and to provide the sample chamber in which the sample to be evaluated is housed.

FIGS. 3A-3C illustrates one of these test strips (see U.S. Pat. No. 6,942,518, which is assigned to the same assignee as the present application, and is hereby incorporated by reference). This configuration is used for side-filling, and end-filling is an alternative. FIG. 3A illustrates a first substrate 340 with a working electrode 342. FIG. 3B illustrates a spacer 344 defining a channel 346. FIG. 3C (inverted with respect to FIGS. 3A and 3B) illustrates a second substrate 348 with three counter (or counter/reference) electrodes 350, 352, 354. This multiple counter electrode arrangement can provide a fill indicator function, as described below. The length of the channel 346 is typically defined by the two parallel cuts along the sides 356, 358 of the sensors.

Glucose test strip sensors can be manufactured adjacent to one another, as illustrated in FIGS. 4A-4B. Such positioning during manufacture produces less waste material. This often results in better efficiency as compared to other techniques, such as individually placing components within the individual channels of test strip sensors.

General Method for Manufacturing Glucose Sensors

FIGS. 4A-4B illustrate the processing of a sheet 1000 of test strips. Referring now to FIGS. 4A and 4B, one example of a method for making thin film sensors is generally described, and can be used to make a variety of sensor arrangements. When the three layers of the test strips of FIGS. 3A-3C, e.g., are assembled, a sensor is formed.

In FIGS. 4A and 4B, a substrate 400, such as a plastic substrate, is moving in the direction indicated by the arrow. The substrate 400 can be an individual sheet or a continuous roll on a web. Multiple sensors can be formed on a substrate 400 as sections 422 that have working electrodes thereon and sections 424 that have counter electrodes and indicator electrodes thereon. These working, counter and indicator electrodes are electrically connected to corresponding traces and contact pads. Typically, working electrode sections 422 are produced on one half of substrate 400 and counter electrode sections 424 are produced on the other half of substrate 400. In some embodiments, the substrate 400 can be scored and folded to bring the sections 422, 424 together to form the sensor. In some embodiments, as illustrated in FIG. 4A, the individual working electrode sections 422 can be formed next to or adjacent each other on the substrate 400, to reduce waste material. Similarly, individual counter electrode sections 424 can be formed next to or adjacent each other. In other embodiments, the individual working electrode sections 422 (and, similarly, the counter electrode sections 424) can be spaced apart, as illustrated in FIG. 4B.

Radio Frequency Identification (RFID)

RFID provides an advantageous technology for remotely storing and retrieving data using devices called RFID tags. A RFID tag is a small object, such as an adhesive sticker, that can be attached to or incorporated into a product. There are passive and active RFID tags. Passive RFID tags are small devices that are generally used at shorter range and for simpler tracking and monitoring applications than active tags. Passive tags generally act over ranges up to 3-5 meters, and a few hundred are typically readable simultaneously within three meters of a reader. Because they are powered by radio waves from RFID tag reader, passive tags do not use a battery. Therefore these devices are generally inexpensive and smaller than active tags, and can last long. Active RFID tags have a power source, such as a battery, and generally have longer range and larger memories than passive tags. For example, active tags generally act over ranges up to 100 meters, and thousands of tags are typically readable simultaneously within 100 meters of a reader. For more details on passive and active RFID tags, see http://RFID-Handbook.com, which is hereby incorporated by reference.

RFID System

An RFID system generally includes a RFID tag and RFID reader. A RFID tag includes an antenna and digital memory chip. A RFID reader, also called an interrogator, includes an antenna and a transceiver, and emits and receives RF signals. RFID readers can read tags and can typically write data into the tags. For example, FIG. 5 schematically illustrates component circuitry of a passive RFID tag. A transceiver/receiver 502 of a RFID reader 505 is directionally coupled 504 to an antenna 506 of the reader 505. An RFID transponder 510 includes an antenna 512 (e.g., a dipole antenna) and memory 514.

It is desired to incorporate RFID tag technology into glucose test strips, test strip vials and/or boxes of strips. It is also desired to incorporate RFID reader into glucose meters.

SUMMARY OF THE INVENTION

A glucose monitoring system includes a glucose sensor strip or package of strips. The strip includes a substrate and a glucose monitoring circuit that has electrodes and a bodily fluid application portion of selected chemical composition. An antenna is integrated with the glucose sensor strip. A RFID sensor chip is coupled with the glucose sensor strip and the antenna. The chip has a memory containing digitally-encoded data representing calibration and/or expiration date information for the strip.

The antenna may be a loop antenna that has a conducting loop extending around substantially a perimeter of the substrate and has two ends coupled with the chip. A RFID reader may read, power and/or program the chip. The RFID reader may be integrated with a glucose meter that has a port for inserting the strip and measuring a glucose level. Alternatively, a glucose meter may include a RFID reader as a component. The calibration and/or expiration date data may be automatically read when the strip is inserted into the port of the glucose meter. The chip may include a battery or other power source, or may be a passive chip. The memory may also contain data representing a lot number of the strip, manufacture date for the strip, a type of strip, and/or a calibration code. The RFID sensor chip may operate at 13.56 MHz. The calibration data may include chemical composition information for the strip for accurately computing a glucose level based on the chemical composition.

BRIEF DESCRIPTION OF THE DRAWINGS

FIGS. 3A-3C illustrate a conventional test strip.

DETAILED DESCRIPTION OF THE PREFERRED EMBODIMENTS

A RFID sensor is advantageously coupled with a blood glucose test strip or with a group of strips in accordance with a preferred embodiment. The RFID sensor preferably includes calibration and/or expiration date information for the strips. The calibration information preferably includes information relating to the chemical composition of the strip, so that a blood glucose reading can be accurately computed from a reading obtained using the strip with the particular chemical composition.

Figure 6:
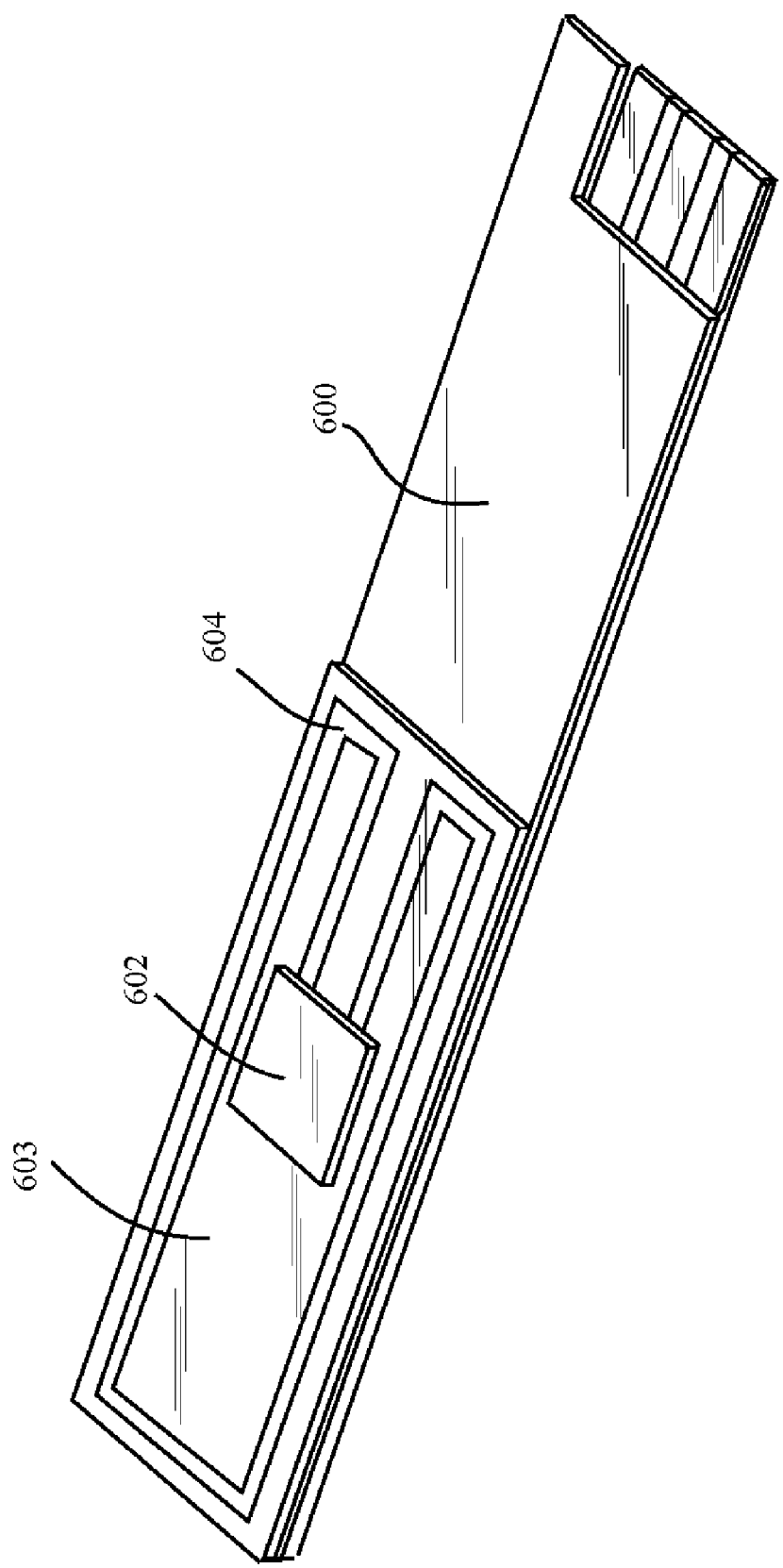
FIG. 6 illustrates a glucose test strip including a RFID chip and antenna in accordance with a preferred embodiment.

In one embodiment, an individual strip includes a RFID sensor. FIG. 6 illustrates a glucose test strip 600, e.g., a Freestyle® test strip manufactured by Abbott Diabetes Care of Alameda, Calif., that includes a RFID chip 602, which is mounted on a PCB substrate 603 or other suitable substrate, and an antenna 604, in accordance with a preferred embodiment. The antenna 604 may be a loop antenna, or a dipole antenna, or another antenna configuration.

Figure 7:
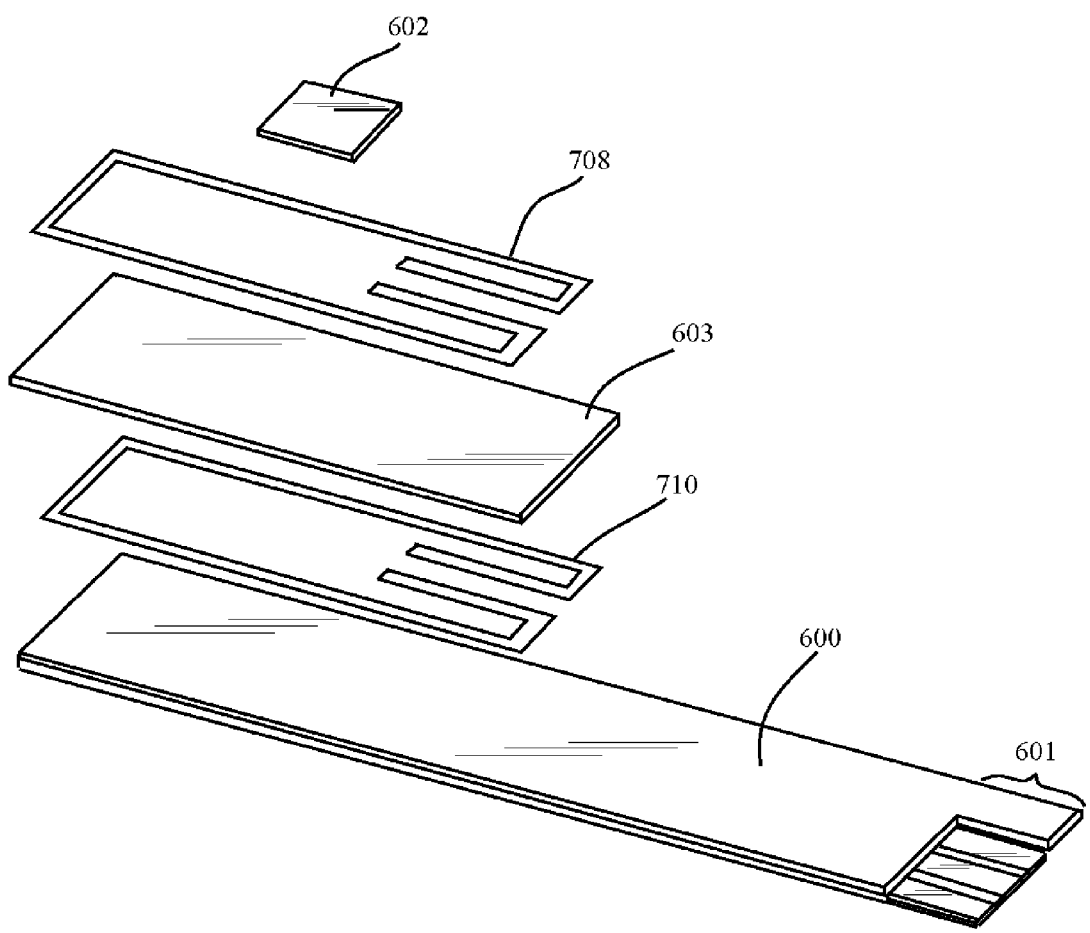
FIG. 7 is an exploded view of a glucose test strip in accordance with a preferred embodiment.
Figure 8:
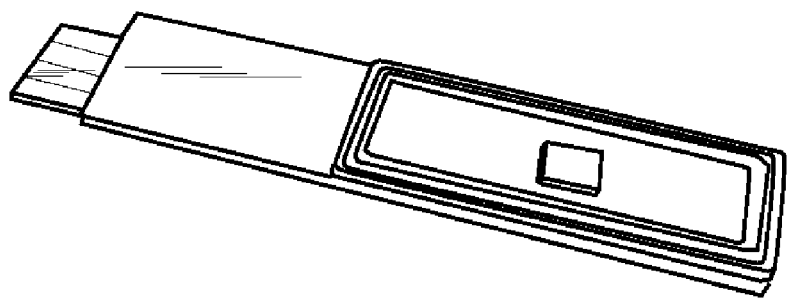
FIG. 8 illustrates a RFID chip mounted on a glucose test strip in accordance with a preferred embodiment.

FIG. 7 is an exploded view of a Freestyle® or other glucose test strip 600 including a sample application end 601, with sample chamber and electrodes, a RFID chip 602 in accordance with a preferred embodiment. The RFID chip 602 is mounted on a PCB substrate 603 that is attached to, integral with or part of the strip 600. There is a top-side loop antenna 708 and a bottom side loop antenna 710. FIG. 8 illustrates a RFID chip 602 mounted on a glucose test strip 600 in accordance with another embodiment.

Figure 9:
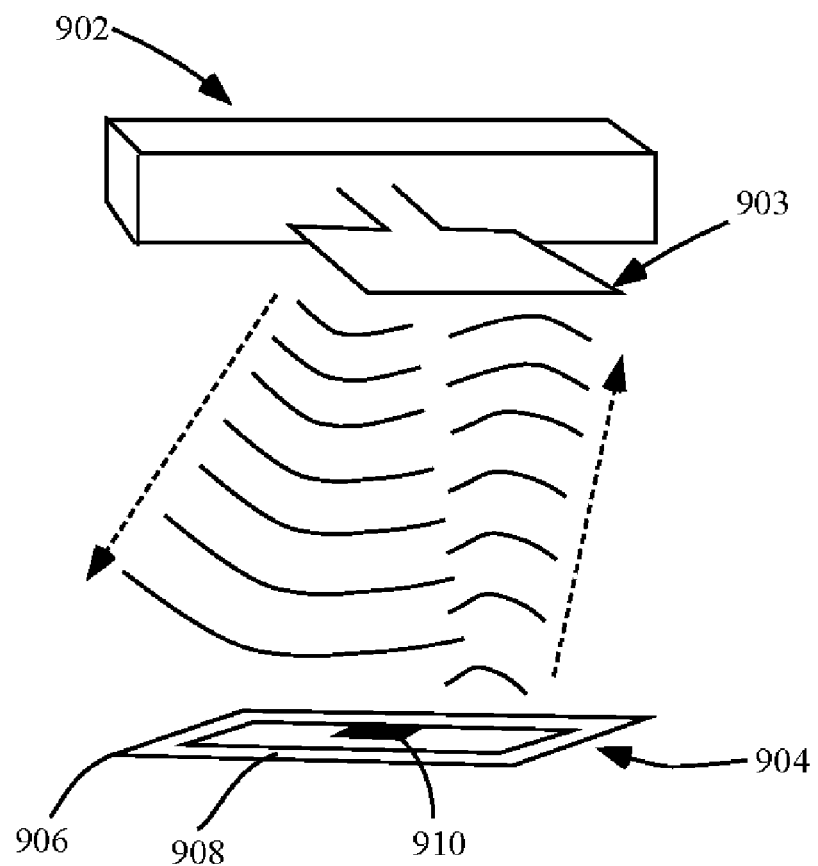
FIG. 9 illustrates a communication system including a glucose test strip and a RFID reader in accordance with a preferred embodiment.

Preferably a RFID reader programs the RFID sensor with the calibration data and/or powers the RFID sensor. The RFID reader may be integrated with a blood glucose meter, or the meter may include an RFID reader as a component. FIG. 9 illustrates a communication system including a RFID reader 902 and a tag 904 in accordance with a preferred embodiment. The reader 902 includes a reader antenna 903. The tag 904 may be coupled with a glucose test strip or with a package or box of strips. The tag 904 includes a substrate 906, tag antenna 908 and RFID chip 910. The reader 902 sends a radio wave that impinges upon the tag 904. A backscattering radio wave is propagated back from the tag 904 as a result.

Figure 10:
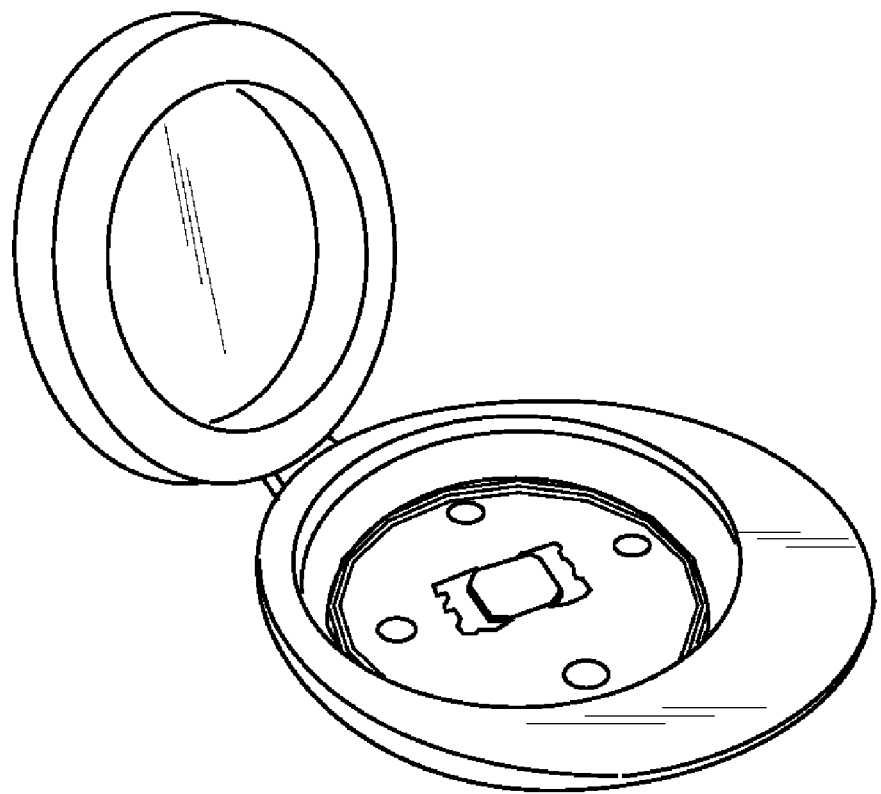
FIG. 10 illustrates a RFID chip mounted on a package for holding glucose test strips in accordance with a preferred embodiment.

FIG. 10 illustrates a RFID chip mounted on a package for holding glucose test strips in accordance with a preferred embodiment. The package illustrated is a lid of a vial container of several tens of test strips. Preferably, each of the test strips in the vial was manufactured on a same sheet of strips, such that the chemical compositions of the strips are very similar and that the strips have a common expiration date.

Meters Equipped with a RFID Tag Reader (or Vice-Versa)

In accordance with another advantageous embodiment, a RFID tag reader or interrogator may be adapted for providing glucose testing. As such, a test strip receptacle and glucose measurement circuitry and/or programming may be provided in a glucose meter module that plugs into a RFID reader device or is integrated therein or otherwise communicates data and/or power by cable or multi-pin connection, or wirelessly (at least for the data communication) with the RFID reader. The glucose meter module can use the power and processing capabilities of the reader, thus streamlining the meter module compared with a stand-alone meter. Even data storage for both the reader and meter may be combined into one location or otherwise synchronized.

In another embodiment, a glucose meter may be adapted for providing RFID reading and/or writing. A RFID reader may be provided that plugs into a glucose meter or is integrated therein or otherwise communicates data and/or power by cable, or multi-pin connection, or wirelessly (at least for the data communication) with the glucose meter. The RFID reader can use the power and processing capabilities of the meter, thus streamlining the RFID reader module compared with a stand-alone reader. Even data storage for both the reader and meter may be combined into one location or otherwise synchronized.

Human errors are advantageously prevented by automatically retrieving a calibration code of one or more test strips stored in a RFID tag. Expiration date information for the test strip can also be detected from the tag. Different types of test strips can also be detected, which is advantageous particularly for different strips that appear alike and/or that may be used with a same piece of diabetes care equipment. Several other possible types of data may be stored in and read from a RFID tag, which may used alone and/or may be combined with other diabetes care data to enhance the reliability of a diabetes treatment regimen, including the recording, retrieval and/or use of relevant data (see, e.g., U.S. patent application Ser. Nos. 10/112,671 and 11/146,897, which are assigned to the same assignee and are hereby incorporated by reference). Embodiments disclosed in the Ser. No. 10/112,671 application, and in U.S. Pat. Nos. 5,899,855, 5,735,285, 5,961,451, 6,159,147 and 5,601,435, which are hereby incorporated by reference, describe alternative arrangements for combining functionalities of devices that may be modified for use with an advantage glucose meter and RFID reader combination in accordance with a preferred embodiment.

Figure 11:
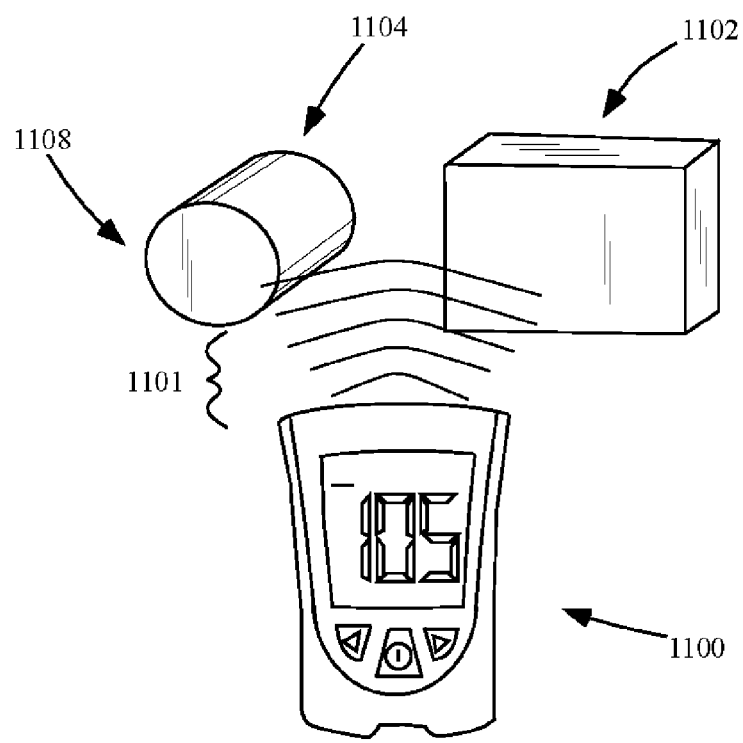
FIG. 11 illustrates a glucose meter communicating with a RFID tag that is mounted on a package or box of glucose test strips in accordance with a preferred embodiment.

FIG. 11 illustrates a glucose meter 1100 sending radio waves 1101 for communicating with a RFID tag (not specifically shown) that is mounted on a package such as a vial 1104 or a box 1106 of glucose test strips in accordance with preferred embodiments. In a first embodiment, a RFID sensor is coupled with a package or vial container 1104 of glucose test strips. The container 1104 may have a lid 1108 with the RFID sensor attached on its inside surface, or embedded therein, or mounted on the outside with a protective layer affixed over it, or alternatively on the bottom of the container 1104 or otherwise. In another embodiment, the strips are contained within a box 1102 having a RFID tag mounted preferably on the inside of the box to protect the tag, or alternatively on the outside having a protective layer over it.

Figure 12:
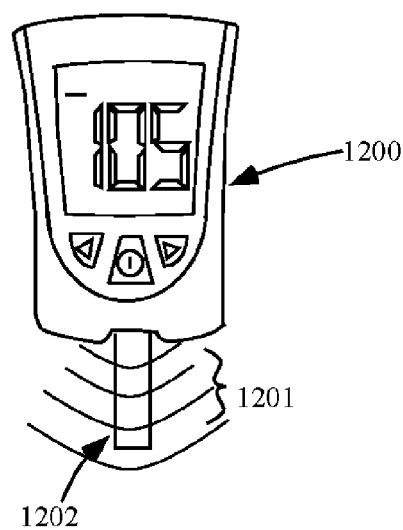
FIG. 12 illustrates a glucose meter communicating with a RFID tag that is mounted on a glucose test strip in accordance with a preferred embodiment.

Containers 1102 or 1104 preferably include only strips from a same sheet of strips having same or similar chemical compositions and expiration dates. One strip may be tested from the sheet, while the remaining strips are placed into the container. The rest of the strips that are placed in the container and not tested will reliably have the same or very similar chemical composition as the tested strip. The RFID sensor may be read only, or may also be write programmable. The data contained within the memory of the RFID sensor preferably includes calibration data regarding the chemical compositions of the strips in the container 1102, 1104 which are each estimated to have the same chemical composition as the test strip, and expiration date data for the strips, which should be the same for all of the strips that were manufactured on the same sheet at the same time. In accordance with another embodiment, FIG. 12 illustrates a glucose meter 1200 communicating with a RFID tag using radio waves 1201 that is mounted on a glucose test strip 1202 in accordance with a preferred embodiment.

RFID Frequency Band Allocation

Multiple frequency bands are available for RFID communication in accordance with preferred embodiments. For example, there is a low frequency band around 125 kHz-134 kHz. There is a worldwide standard high frequency band around 13.56 MHz. There are also UHF frequency bands around 868 MHz for European Union countries, and around 902 MHz-928 MHz for the United States. There is also a microwave frequency band around 2.45 GHz.

It is preferred to use the worldwide standard around 13.56 MHz as the frequency band of operation in accordance with a preferred embodiment. This is the most popular frequency band, and a silicon-based RFID chip operating at this frequency band may be provided at low cost. This frequency band has a high efficiency RF energy transition, and complies with a world-wide RF standard.

Test Strip Coding and Meter Calibrating

Test strip coding and meter calibrating are the processes by which a blood glucose meter is matched with the reactivity of the test strips. A glucose meter will calculate a glucose level of a fluid applied to a strip based on a predetermined chemical composition of the strip. If the predetermined composition varies from the actual composition, then glucose test results provided by the meter will also vary from actual glucose levels.

Figure 1:
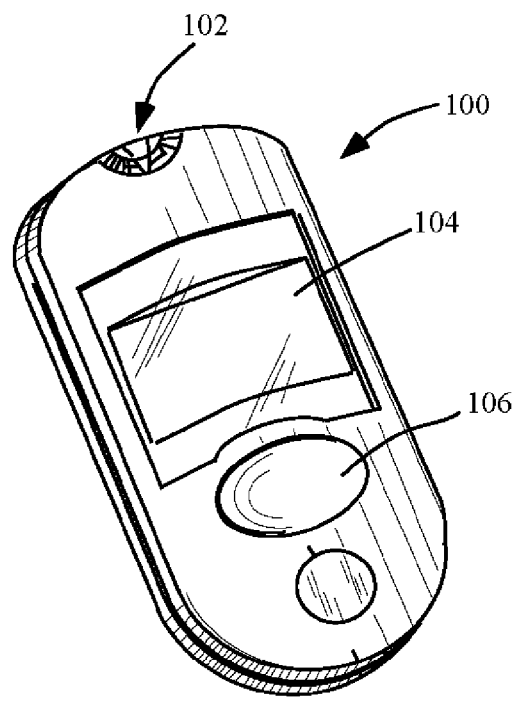
FIG. 1 illustrates a conventional blood glucose meter.
Figure 2:
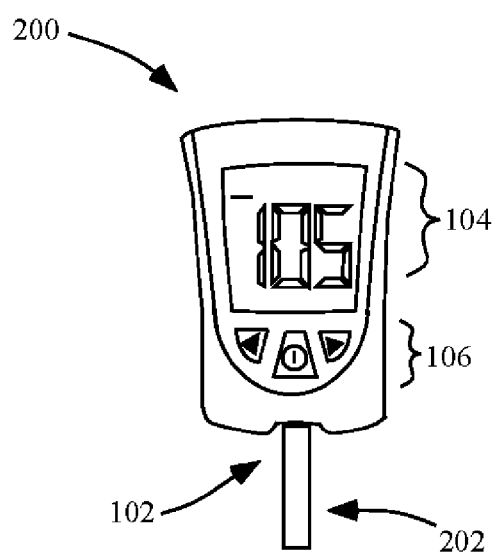
FIG. 2 illustrates a blood glucose meter having a strip inserted into a slot for testing a body fluid sample applied to the strip.
Figure 4A:
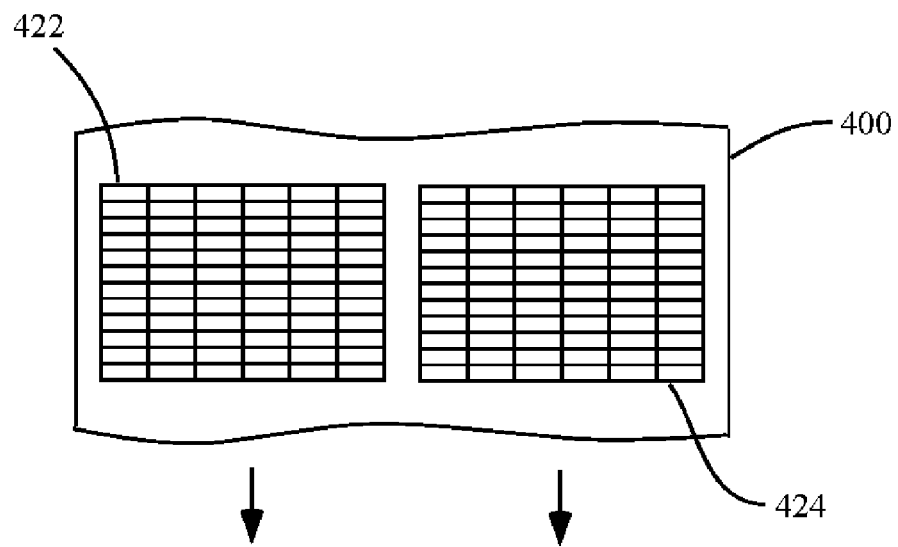
FIGS. 4A-4B illustrate the processing of a sheet of test strips.
Figure 4B:
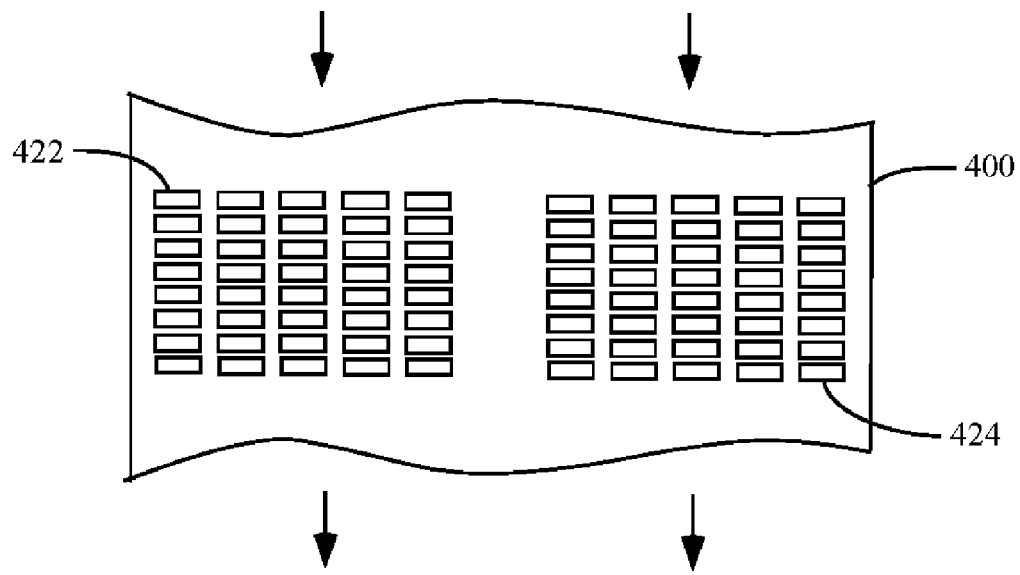
Figure 5:
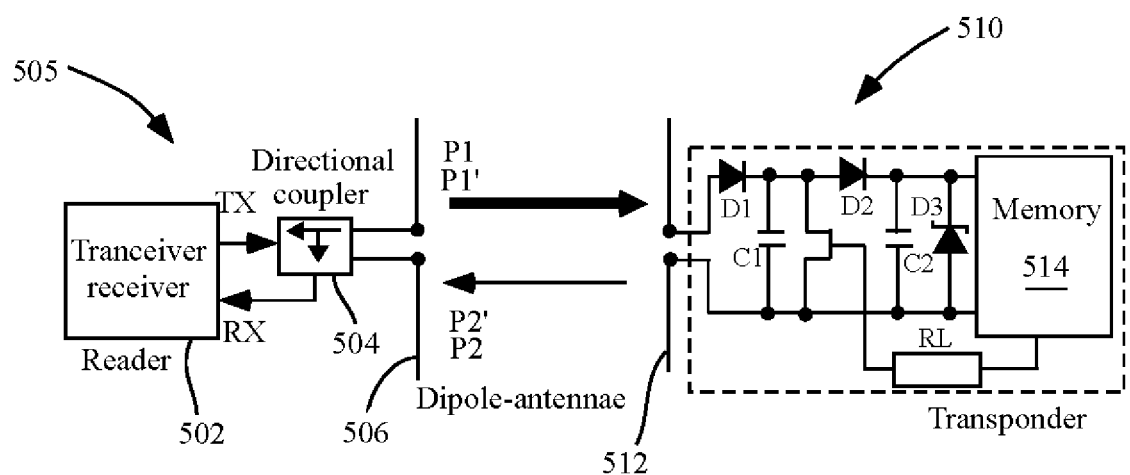
FIG. 5 illustrates a conventional passive RFID tag.

Even test strips intended to be manufactured with a same chemical composition can vary based on uncertainties in the manufacturing process. Although this variance may be only very small when great care is taken in the manufacturing process, these very small variances can alter glucose measurement results that are output by a glucose meter from actual values unless the meter is properly calibrated. As illustrated at FIGS. 4A-4B and described briefly above, multiple test strips are advantageously manufactured together on a same sheet. Test strips that are manufactured on a same sheet have reduced variances in chemical composition compared with test strip manufactured separately. Therefore, one strip from a sheet is advantageously tested in accordance with a preferred embodiment to determine its precise composition. Then, blood glucose meters are calibrated according to that composition when utilizing other strips from that same sheet for testing. As a consequence, glucose testing results are more reliably precise and accurate.

To ensure this precision and accuracy of glucose test results using blood glucose meters in accordance with a preferred embodiment, the strips may be coded, e.g., by the strip manufacturer before they are shipped out. In addition, the glucose meter is calibrated. Calibration of the meter can be performed by inserting a code strip into the meter and executing a calibration routine. The Precision™ meter of Abbott Diabetes Care® preferably uses this technique. Another method of calibration can be performed by entering a code number into the meter. This technique is preferred for use with the Freestyle® meter also of Abbott Diabetes Care®. Advantageously, the encoded calibration data can be stored in the RFID chip described above that is affixed to a strip, or a vial, box or other container of strips. Enhanced efficiency and reliability is achieved whether an RFID chip is mounted to each strip or to a vial, box or other container of strips. However, when the RFID chip from which the encoded calibration data is read is affixed to the vial, box or other container of strips, and preferably all of the strips within that vial, box or other container were manufactured from the same sheet of strips, as described above, then even greater efficiency, i.e., programming and use of a reduced number of RFID chips, is achieved. Advantageously, one RFID chip may be used for initially programming and for later obtaining calibration data for multiple strips. Moreover, expiration date data may be stored and obtained in RFID chips with the same efficiencies and advantages.

It is preferred to provide passive RFID tags on test strips, vials, boxes and/or other containers of strips. The preferred passive RFID tags can store approximately two kilobytes of data or more. The memory of the passive tag can be read and written repeatedly. In the memory, the following are preferably stored: test strip calibration codes, lot number, manufacture date, expiration date, other calibration information, or type of strip, or combinations thereof.

By using RFID tags, a test strip manufacturing process is advantageously upgraded. IN this embodiment, test strips are manufactured and preferably packed directly into final packages in vials or boxes or other containers, instead of waiting, e.g., for two weeks, for labeling of calibration codes. The calibration codes are preferably written into the RFID tags after the codes are determined. A lot group size of the test strips can be broken into a smaller geometry to achieve a more precise uniformity of chemical reactivity code. Further data can be stored into RFID tags, as desired.

The calibration, expiration date and/or other diabetes care information may be provided in a RFID chip or module associated with glucose sensors other than test strips and test strip containers. For example, continuous glucose sensors that may be implanted or partially in vivo or otherwise can include RFID features described otherwise herein. In addition, diabetes care devices other than glucose sensors such as insulin pumps can use the RFID communication of data such as pump calibration data, insulin infusion data, computed or received dose data or glucose data available at the pump. As to the latter feature, glucose data may be communicated to a pump by a glucose meter, and then read by a RFID reader.

The present invention is not limited to the embodiments described above herein, which may be amended or modified without departing from the scope of the present invention as set forth in the appended claims, and structural and functional equivalents thereof.

In methods that may be performed according to preferred embodiments herein and that may have been described above and/or claimed below, the operations have been described in selected typographical sequences. However, the sequences have been selected and so ordered for typographical convenience and are not intended to imply any particular order for performing the operations.

In addition, all references cited above herein, in addition to the background and summary of the invention sections, are hereby incorporated by reference into the detailed description of the preferred embodiments as disclosing alternative embodiments and components.

What is claimed is:

1. A glucose monitoring system, comprising:
   (a) a glucose sensor comprising a strip, including:
      (i) a substrate; and
      (ii) a glucose monitoring circuit having multiple electrodes and a bodily fluid application portion of selected chemical composition;
   (b) an antenna integrated with the glucose sensor;
   (c) a RFID sensor chip coupled with the glucose sensor and the antenna, wherein the chip comprises a memory containing digitally-encoded data representing expiration date information for the sensor; and
   (d) a RFID reader integrated with a glucose meter that has a port for inserting the glucose sensor strip and measuring a glucose level, wherein the RFID reader is for reading, programming or powering the chip, or combinations thereof, and
   (e) wherein the expiration date data is automatically read from the RFID sensor chip by the RFID reader by RF communication when the strip is inserted into the port of the glucose meter.

2. The system of claim 1, wherein the antenna comprises a loop antenna.

3. The system of claim 2, wherein the loop antenna comprises a conducting loop extending around substantially a perimeter of the substrate and having two ends coupled with the chip.

4. The system of claim 1, wherein the RFID reader is further for powering the chip.

5. The system of claim 1, wherein the RFID reader is further for programming the chip.

6. The system of claim 1, wherein the chip comprising a battery or other power source.

7. The system of claim 1, wherein the memory further contains data representing a lot number of the glucose sensor strip, manufacture date for the strip, a type of strip or other sensor, or a calibration code or other calibration data, or combinations thereof.

8. The system of claim 1, wherein the RFID sensor chip operates at 13.56 MHz.

9. The system of claim 1, wherein the glucose sensor comprises a continuous glucose sensor.

10. A glucose monitoring system, comprising:
    (a) a glucose sensor comprising a strip, including:
       (i) a substrate; and
       (ii) a glucose monitoring circuit having multiple electrodes and a bodily fluid application portion of selected chemical composition;
    (b) an antenna integrated with the glucose sensor;
    (c) a RFID sensor chip coupled with the glucose sensor and the antenna, wherein the chip comprises a memory containing digitally-encoded data representing expiration date information for the sensor,
    (d) a glucose meter including a RFID reader component for reading, programming or powering the chip, or combinations thereof wherein the glucose meter comprises a port for inserting the glucose sensor strip and measuring a glucose level, and
    (e) wherein the expiration date data is automatically read by the glucose meter by RF communication when the strip is inserted into the port of the glucose meter.

11. The system of claim 10, wherein the memory further contains data representing a lot number of the glucose sensor strip, manufacture date for the strip, a type of strip or other sensor, or a calibration code or other calibration data, or combinations thereof.

12. The system of claim 10, wherein the antenna comprises a conducting loop extending around substantially a perimeter of the substrate and having two ends coupled with the chip.

13. The system of claim 10, wherein the glucose sensor comprises a continuous glucose sensor.

14. A glucose monitoring system, comprising:
    (a) a glucose sensor comprising a strip, including:
       (i) a substrate; and
       (ii) a glucose monitoring circuit having multiple electrodes and a bodily fluid application portion of selected chemical composition;
    (b) an antenna integrated with the glucose sensor;
    (c) a RFID sensor chip coupled with the glucose sensor and the antenna, wherein the chip comprises a memory containing digitally-encoded data representing calibration information for the sensor; and
    (d) a RFID reader integrated with a glucose meter that has a port for inserting the glucose sensor strip and measuring a glucose level, wherein the RFID reader is for reading, programming or powering the chip, or combinations thereof, and
    (e) wherein the calibration data is automatically read by RF communication when the strip is inserted into the port of the glucose meter.

15. The system of claim 14, wherein the antenna comprises a loop antenna.

16. The system of claim 15, wherein the loop antenna comprises a conducting loop extending around substantially a perimeter of the substrate and having two ends coupled with the chip.

17. The system of claim 15, wherein the RFID reader is further for powering the chip.

18. The system of claim 15, wherein the RFID reader is further for programming the chip.

19. The system of claim 15, wherein the chip comprising a battery or other power source.

20. The system of claim 15, wherein the memory further contains data representing a lot number of the glucose sensor strip, manufacture date for the strip, a type of strip or other sensor, a calibration code or expiration date data, or combinations thereof.

21. The system of claim 15, wherein the RFID sensor chip operates at 13.56 MHz.

22. The system of claim 15, wherein the calibration data includes chemical composition information for the glucose sensor strip for accurately computing a glucose level based on said chemical composition.

23. The system of claim 15, wherein the glucose sensor comprises a continuous glucose sensor.

24. A glucose monitoring system, comprising:
 (a) a glucose sensor comprising a strip, including:
  (i) a substrate; and
  (ii) a glucose monitoring circuit having multiple electrodes and a bodily fluid application portion of selected chemical composition;
 (b) an antenna integrated with the glucose sensor;
 (c) a RFID sensor chip coupled with the glucose sensor and the antenna, wherein the chip comprises a memory containing digitally-encoded data representing calibration information for the sensor;
 (d) a glucose meter including a RFID reader component for reading, programming or powering the chip, or combinations thereof,
 (e) wherein the glucose meter comprises a port for inserting the glucose sensor strip strip and measuring a glucose level, and wherein the calibration data is automatically read by the RFID reader component by RF communication when the strip is inserted into the port of the glucose meter.

25. The system of claim 24, wherein the memory further contains data representing a lot number of the glucose sensor strip, manufacture date for the strip, a type of strip or other sensor, or a calibration code or other calibration data, or combinations thereof.

26. The system of claim 24, wherein the antenna comprises a conducting loop extending around substantially a perimeter of the substrate and having two ends coupled with the chip.

27. The system of claim 24, wherein the glucose sensor comprises a continuous glucose sensor.

28. A glucose monitoring system, comprising:
 (a) a package of glucose sensor strips, the strips each including:
  (i) a substrate; and
  (ii) a glucose monitoring circuit having multiple electrodes and a bodily fluid application portion of selected chemical composition;
 (b) an antenna integrated with the package; and
 (c) a RFID sensor chip coupled with the package and the antenna, wherein the chip comprises a memory containing digitally-encoded data representing expiration date information for the strip;
 (d) a RFID reader integrated with a glucose meter that has a port for inserting one of the strips and measuring a glucose level, wherein the a RFID reader is for reading, programming or powering the chip, or combinations thereof, and
 (e) wherein the expiration date data is automatically read by the RFID reader by RF communication when one of the strips is inserted into the port of the glucose meter.

29. The system of claim 28, wherein the antenna comprises a loop antenna.

30. The system of claim 29, wherein the loop antenna comprises a conducting loop extending around substantially a perimeter of the substrate and having two ends coupled with the chip.

31. The system of claim 28, wherein the RFID reader is further for powering the chip.

32. The system of claim 28, wherein the RFID reader is further for programming the chip.

33. The system of claim 28, wherein the chip comprising a battery or other power source.

34. The system of claim 28, wherein the memory further contains data representing a lot number of the strips, manufacture date for the strips, a type of the strips, or a calibration code or other calibration data, or combinations thereof.

35. The system of claim 28, wherein the RFID sensor chip operates at 13.56 MHz.

36. A glucose monitoring system, comprising:
 (a) a package of glucose sensor strips, the strips each including:
  (i) a substrate; and
  (ii) a glucose monitoring circuit having multiple electrodes and a bodily fluid application portion of selected chemical composition;
 (b) an antenna integrated with the package; and
 (c) a RFID sensor chip coupled with the package and the antenna, wherein the chip comprises a memory containing digitally-encoded data representing expiration date information for the strip;
 (d) a glucose meter including a RFID reader component for reading, programming or powering the chip, or combinations thereof, and
 (e) wherein the glucose meter comprising a port for inserting the strip and measuring a glucose level, and wherein the expiration date data is automatically read by the RFID reader component by RF communication when one of the strips is inserted into the port of the glucose meter.

37. The system of claim 36, wherein the memory further contains data representing a lot number of a glucose sensor strip, manufacture date for the strip, a type of strip or other sensor, or a calibration code or other calibration data, or combinations thereof.

38. The system of claim 36, wherein the antenna comprises a conducting loop extending around substantially a perimeter of the substrate and having two ends coupled with the chip.

39. The system of claim 36, wherein the glucose sensor comprises a continuous glucose sensor.

40. A glucose monitoring system, comprising:
 (a) a package of glucose sensor strips, the strips each including:
  (i) a substrate; and
  (ii) a glucose monitoring circuit having multiple electrodes and a bodily fluid application portion of selected chemical composition;
 (b) an antenna integrated with the package; and
 (c) a RFID sensor chip coupled with the package and the antenna, wherein the chip comprises a memory containing digitally-encoded data representing calibration information for the strip; and
 (d) a RFID reader integrated with a glucose meter that has a port for inserting one of the strips and measuring a glucose level, wherein the a RFID reader is for reading, programming or powering the chip, or combinations thereof, (e) wherein the calibration data is automatically read by the RFID reader by RF communication when one of the strips is inserted into the port of the glucose meter.

41. The system of claim 40, wherein the antenna comprises a loop antenna.

42. The system of claim 41, wherein the loop antenna comprises a conducting loop extending around substantially a perimeter of the substrate and having two ends coupled with the chip.

43. The system of claim 40, wherein the RFID reader is further for powering the chip.

44. The system of claim 40, wherein the RFID reader is further for programming the chip.

45. The system of claim 40, wherein the chip comprises a battery or other power source.

46. The system of claim 40, wherein the memory further contains data representing a lot number of the strips, manufacture date for the strips, a type of the strips, a calibration code or expiration date data, or combinations thereof.

47. The system of claim 40, wherein the RFID sensor chip operates at 13.56 MHz.

48. The system of claim 40, wherein the calibration data includes chemical composition information for the strips for accurately computing a glucose level based on said chemical composition.

49. A glucose monitoring system, comprising:
 (a) a package of glucose sensor strips, the strips each including:
  (i) a substrate; and
  (ii) a glucose monitoring circuit having multiple electrodes and a bodily fluid application portion of selected chemical composition;
 (b) an antenna integrated with the package; and
 (c) a RFID sensor chip coupled with the package and the antenna, wherein the chip comprises a memory containing digitally-encoded data representing calibration information for the strip; and
 (d) a glucose meter including a RFID reader component for reading, programming or powering the chip, or combinations thereof, and
 (e) wherein the glucose meter comprising a port for inserting one of the strips and measuring a glucose level, and wherein the calibration data is automatically read by the RFID reader component by RF communication when one of the strips is inserted into the port of the glucose meter.

50. The system of claim 49, wherein the memory further contains data representing a lot number of a glucose sensor strip, manufacture date for the strip, a type of strip or other sensor, or a calibration code or other calibration data, or combinations thereof.

51. The system of claim 49, wherein the antenna comprises a conducting loop extending around substantially a perimeter of the substrate and having two ends coupled with the chip.

52. The system of claim 49, wherein the glucose sensor comprises a continuous glucose sensor.

* * * * *

UNITED STATES PATENT AND TRADEMARK OFFICE
CERTIFICATE OF CORRECTION

PATENT NO.        : 7,545,272 B2
APPLICATION NO.   : 11/350398
DATED             : June 9, 2009
INVENTOR(S)       : Timothy T. Goodnow It is certified that error appears in the above-identified patent and that said Letters Patent is hereby corrected as shown below:

Claim 24, column 9, line 35: Following "strip" delete the duplicate "strip".

Signed and Sealed this

Thirteenth Day of October, 2009

David J. Kappos
*Director of the United States Patent and Trademark Office*